United States Patent
Sakashita (10) Patent No.: US 6,354,724 B1
(45) Date of Patent: Mar. 12, 2002

(54) LINE ILLUMINATING APPARATUS

(75) Inventor: Shigeji Sakashita, Tokyo (JP)

(73) Assignee: Kokusai Gijutsu Kaihatsu Co., Ltd., Tokyo (JP)

( * ) Notice: Subject to any disclaimer, the term of this patent is extended or adjusted under 35 U.S.C. 154(b) by 0 days.

(21) Appl. No.: 09/512,770

(22) Filed: Feb. 25, 2000

(30) Foreign Application Priority Data

Mar. 16, 1999 (JP) .......................................... 11-070558

(51) Int. Cl.[7] .............................. F21V 11/00; G02B 5/02
(52) U.S. Cl. ..................................... 362/558; 356/402
(58) Field of Search ................................. 362/558, 554, 362/551, 31, 575, 327; 356/402, 446, 237; 348/426

(56) References Cited

U.S. PATENT DOCUMENTS

| | | |
|---|---|---|
| 4,677,473 A | 6/1987 | Okamoto et al. |
| 4,922,109 A | 5/1990 | Bercovitz et al. |
| 5,153,668 A | * 10/1992 | Katzir et al. ............... 356/237 |
| 5,243,402 A | 9/1993 | Weber et al. |
| 5,274,713 A | 12/1993 | Chang et al. |

OTHER PUBLICATIONS

European Search Report No. 00 10 5480.

* cited by examiner

Primary Examiner—Alan Cariaso
Assistant Examiner—Bao Truong
(74) Attorney, Agent, or Firm—Oliff & Berridge, PLC.

(57) ABSTRACT

A line illuminating apparatus comprises a pair of irradiating units 12a, 12b of the same structure. The irradiating unit 12a. The light irradiating unit 12a includes a light source 14a, a first light guide 16a consisting of a large number of optical fibers, a light connector 18a, and three second light guides 20 (20a to 20c). The first light guide 16a permits the light emitted from the light source 14a to be incident as a slender rectangular light ray on the light connector 18a. The light emitted from the light connector 18a is divided by the three second light guides 20. Each light guide 20 is in the form of a thin plate, and the light emitting surfaces of the light guides 20a to 20f are arranged to define a imaginary semicylindrical plane surrounding the irradiating line L of work 28. The particular construction is effective for suppressing the loss of energy required for illumination. Also, the inspection is not adversely affected by the presence of, for example, an irregularity on the surface of the work.

10 Claims, 5 Drawing Sheets

LINE ILLUMINATING APPARATUS

TECHNICAL FIELD

The present invention relates to a line illuminating apparatus for illuminating a linear region, particularly, to a line illuminating apparatus adapted for automatically inspecting a fine object to be inspected by utilizing an image processing technology.

BACKGROUND ART

In recent years, an inspection utilizing an image processing technology is widely employed. Particularly, in the case of inspecting a circuit pattern formed on a semiconductor chip, a liquid crystal glass substrate, a printed circuit wiring board, a lead frame for mounting a semiconductor chip or a TAB (Tape Automated Bonding) tape, it is difficult to perform the visual inspection via, for example, a microscope because the pattern has become finer and finer and the mounting density has become higher and higher. Therefore, the target object to be inspected is subjected to an image processing in general to automatically inspect whether or not the line width has a predetermined value.

In a known inspecting apparatus utilizing an image processing technology, a work to be inspected such as a glass substrate, a printed wiring board, or a TAB tape is moved in one direction at a predetermined speed. At the same time, an image of the target object to be inspected such as a circuit pattern is taken in by utilizing a line sensor consisting of, for example, a solid-state pickup device arranged in a direction perpendicular to the moving direction of the work to inspect, for example, the line width by detecting the difference in reflectivity between the substrate such as a base plate or a tape and the pattern. In such a case, an illuminating apparatus for irradiating the work with light is used in order to obtain a clear difference in concentration (difference in brightness) between the substrate and the pattern.

The conventional illuminating apparatus for illuminating a linear inspecting region includes, for example, a linear arrangement of a large number of light-emitting diodes used as a light source, a linear tube-like fluorescent lamp, an apparatus in which the light radiated from a light source is converted into a parallel light by a collimator and the parallel light is, then, converted into a linear light by a cylindrical lens, and another apparatus in which the light radiated from a light source of hundreds of watts is guided by a large number of optical fibers to a region near an illuminating line L, the distal ends of the optical fibers being arranged to form a linear light.

However, the conventional illuminating apparatus having a linear light ray is constructed to illuminate the target object in one direction. Therefore, when viewed from the side of the target object to be illuminated, the brightness differs depending on the viewing direction. For example, where the work has an irregular surface or an opening, bright and dark portions appear in the irregular surface portion. Also, the light is strongly reflected from the edge of the opening to form a bright portion. As a result, it is impossible to perform the inspection, or an erroneous judgment is brought about. Such being the situation, it is necessary to use a dome-shaped illuminating apparatus in which the entire linear illuminating region is covered with a hemispherical member and the entire inner surface of the hemispherical member is allowed to emit light with a uniform brightness. Since the brightness of the dome-shaped illuminating apparatus is isotropic as viewed from the target object, bright and dark portions are not generated, and it is possible to prevent an erroneous inspection result from being derived from the presence of the irregular surface portion.

However, since the dome-shaped illuminating apparatus outlined above uniformly illuminates a very large space, though it suffices to illuminate a small linear region, the loss of energy required for the illumination is very large. In addition, it is difficult to obtain a brightness sufficient for the inspection.

SUMMARY OF THE INVENTION

An object of the present invention, which is intended to overcome the above-noted defects inherent in the prior art, is to provide a line illuminating apparatus that permits suppressing the loss of the energy required for the illumination and also permits preventing the inspection from being affected by the presence of irregularity on the surface of a target object to be inspected.

According to the present invention, there is provided a line illuminating apparatus, comprising a light source and a light guide for guiding the light emitted from the light source to a predetermined irradiating line, wherein the light-emitting surface at the distal end of said light guide is in the form of a semicylinder covering the irradiating line.

It is desirable to divide the semicylindrical plane in the circumferential direction into a plurality of sections each consisting of the light emitting surface of a plate-like light guide. It is also desirable to coarsen the light emitting surface of the light guide to permit the emitted light to be diffused in the axial direction of the semicylindrical plane.

In the line illuminating apparatus of the present invention constructed as described above, the light emitting surfaces of the light guides are arranged to define a imaginary semicylindrical plane extending along the irradiating line. The particular construction makes it possible to make the distance between the irradiating plane to be irradiated and the light emitting planes of the light guides markedly shorter than that in the dome-shaped illuminating apparatus. As a result, the region to be illuminated is diminished to markedly eliminate the energy loss required for the illumination while ensuring the brightness required for the inspection easily and without fail. In addition, since the light emitting surfaces are arranged to define a imaginary semicylindrical plane in a manner to cover the irradiating line, the brightness as viewed from the irradiated plane is rendered isotropic. It follows that, even if an irregularity such as a stepped portion or an opening is present on the work such as a semiconductor substrate, a glass substrate for a liquid crystal display device, a printed wiring board, a lead frame or a TAB tape, it is possible to prevent bright-dark portions from being generated in the irregular portion and to prevent an edge portion of the opening from being strongly reflected, making it possible to eliminate the incapability of inspection and an erroneous inspection.

The light emitted from the light guide has directivity in general, with the result that the intensity of the emitted light tends to be weaker in the peripheral portion than in the central portion of the light emitting surface. For overcoming this difficulty, the semicylindrical plane is divided in the present invention in the circumferential direction into a plurality of sections each consisting of the light emitting surface of the plate-like light guide, making it possible to further improve the isotropy of brightness. Further, since the light emitting surfaces are arranged to define a semicylindrical configuration, the both end portions in the axial direction are rendered dark when viewed from the irradiated surface. To overcome this difficulty, the light emitting surface is coarsened to have anisotropy such that the light emitted from the light emitting surface is diffused in the axial direction of the semicylinder, thereby correcting the darkness in the axial direction of the semicylinder. It follows that it is possible to diminish the influences given by the irregularity or opening present on the work.

LIST OF REFERENCE NUMERALS

10 . . . line illuminating apparatus;
12$a$, 12$b$ . . . irradiating unit;
14$a$ . . . light source;
16$a$ . . . first light guide;
18$a$ . . . light connector;
20$a$ to 20$f$ . . . second light guide;
22 . . . light-emitting surface;
20 28, 56 . . . work;
30 . . . line sensor;
36 . . . image processing section;
38 . . . inspecting section;
60, 70, 80 . . . light guide.

DETAILED DESCRIPTION OF THE PREFERRED EMBODIMENT

A line illuminating apparatus according to a preferred embodiment of the present invention will now be described in detail with reference to the accompanying drawings.

Figure 1:
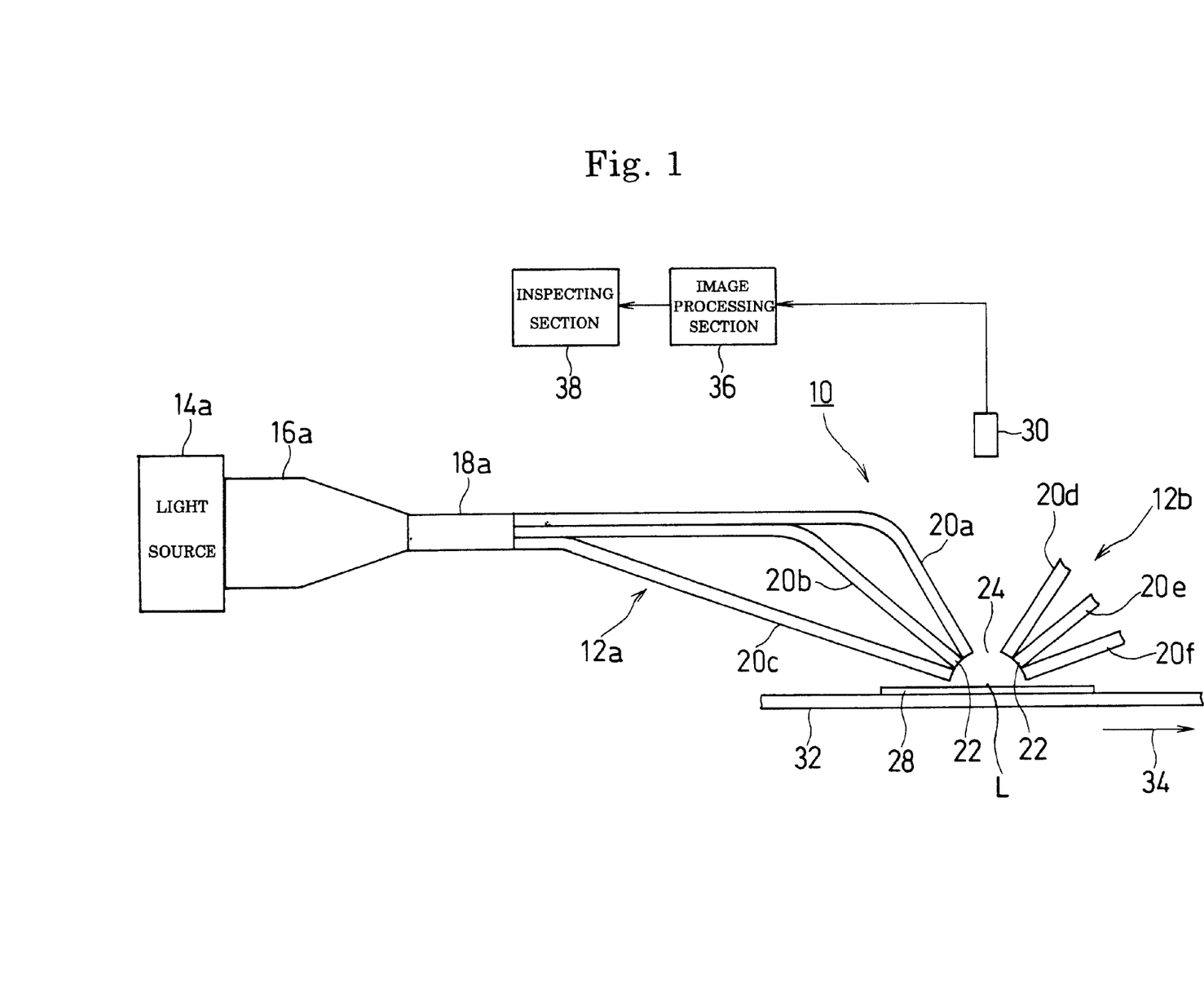
FIG. 1 shows a line illuminating apparatus according to a first embodiment of the present invention.
Figure 2:
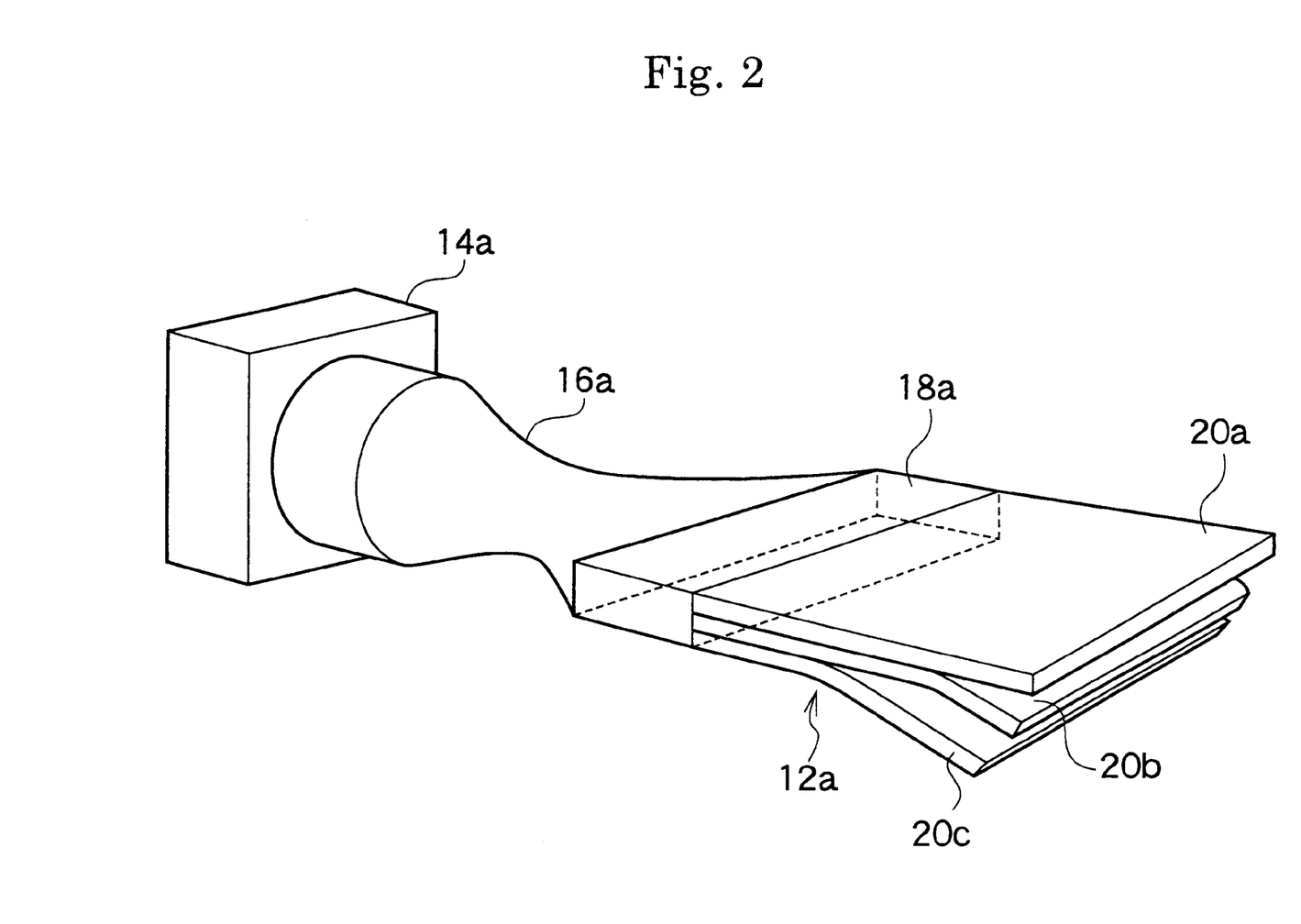
FIG. 2 shows an outer appearance of the light guide portion.

FIG. 1 shows a line illuminating apparatus according to a first embodiment of the present invention, which is used in an automatic inspecting apparatus utilizing an image processing technology. FIG. 2 shows an outer appearance of the light guide portion included in the line illuminating apparatus shown in FIG. 1.

As shown in FIG. 1, a line illuminating apparatus 10 comprises a pair of irradiating units 12 (12$a$, 12$b$). Each of these irradiating units 12$a$ and 12$b$, which are equal to each other in construction, comprises a light source 14 (14$a$, 14$b$), a first light guide 16 (16$a$, 16$b$) consisting of a large number of optical fibers, a light connector 18 (18$a$, 18$b$), and a plurality of second light guides 20 (20$a$ to 22$f$). In this embodiment, three second light guides 20 are included in each of the irradiating units 12. Incidentally, the light source 14$b$ of the irradiating unit 12$b$, the second light guide 16$b$ and the light connector 18$b$ are omitted in FIG. 1.

The light source 14, which consists of, for example, a halogen lamp, radiates light of about 2,000 lumina. The proximal end portion of the first light guide 16, which consists of a large number of optical fibers, on the side of the light source 14 is in the form of, for example, a columnar bundle of the optical fibers. The distal end planes of a large number of optical fibers constituting the first light guide 16 are arranged in a slender rectangular shape extending in a direction perpendicular to the paper. Further, the light connector 18 is in the shape of a plate in which the direction perpendicular to the paper constitutes a longitudinal direction and is formed such that the light incident side edge plane substantially coincides with the light-emitting surface of the first light guide 16. The light connector 18 irregularly reflects in its inner portion the light emerging from the first light guide 16 to permit the light of a predetermined brightness to emerge uniformly from each portion of the light-emitting surface of the light connector 18. Also, the light emitted from the light connector 18 is spectroscopically analyzed by the second light guide 20.

Figure 3:
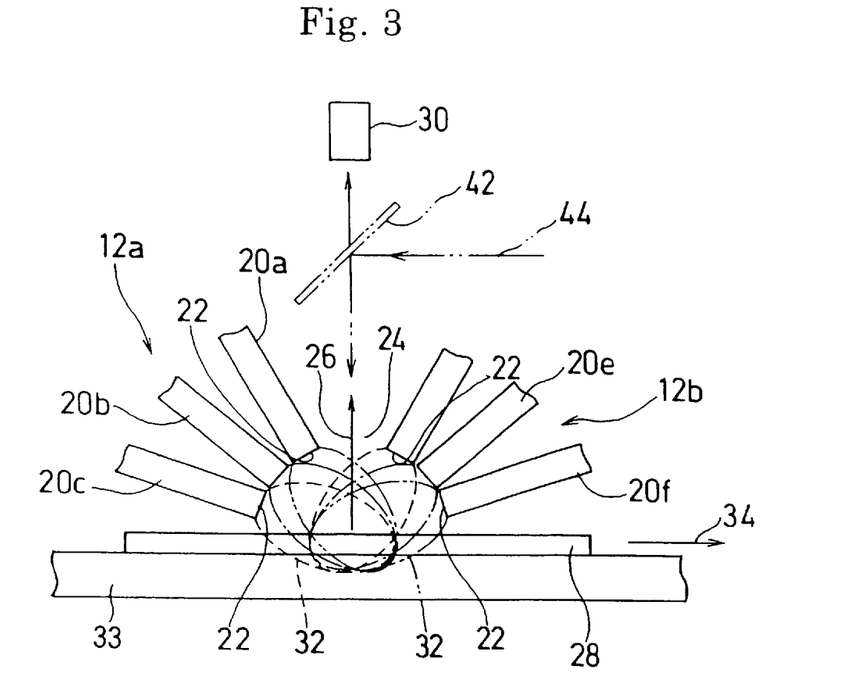
FIG. 3 shows in detail the light emitting portion in the second light guide according to the first embodiment of the present invention.

The second light guide 20 consists of a plurality of thin plate-like second light guides made of a high transparent material such as an acrylic resin or a polycarbonate resin. Also, the up-down direction of the paper in FIG. 1 is a thickness direction of the thin plate-like second light guide. The distal end planes of the thin plate-like second light guides 20$a$ to 120$f$ are arranged on a single circle about an irradiating line L to define a imaginary semicylindrical plane surrounding the irradiating line L. Also, the second light guides 20$a$ to 20$c$ of the first irradiating unit 12$a$ and the second light guides 20$d$ to 20$f$ of the second irradiating unit 12$b$ are substantially equidistantly arranged in the circumferential direction of the semicylindrical plane. It should be noted, however, that a window portion 24 having a predetermined clearance is formed between the second light guide 20$a$ of the first irradiation unit 12$a$ and the second light guide 20$d$ of the second irradiation unit 12$b$ to permit the light 26 reflected from the surface of a work 28, which is a printed wiring board, to be incident on a line sensor 30 arranged above the window portion 24 as shown in FIG. 3. It follows that the second light guides 20$a$ to 20$c$ of the first irradiating unit 12$a$ and the second light guides 20$d$ to 20$f$ of the second irradiating unit 12$b$ are arranged on the left side and right side in symmetry with respect to a plane including the irradiating line L set on the surface of the work 28 and the line sensor 30.

The second light guides 20 are arranged to permit the light-emitting surfaces 22 to cross at right angles the normal lines of the semicylindrical plane such that the optical axes of the light rays 32 emitted from the light-emitting surfaces 22 coincide with a predetermined line on the surface of the work 28, said surface constituting the irradiating line L. As a result, the light rays 32 emitted from the second light guides 20$a$ to 20$f$ and having a directivity are allowed to overlap with each other when viewed from the work 28 and, thus, the brightness is made the same in any direction. In the embodiment shown in the drawing, a circuit pattern to be inspected (not shown) has a line width of about 3 $f\hat{E}m$. The semicylindrical plane defined by the arrangement of the light-emitting surfaces 22 has a radius of 0.5 to 1.5 mm. Further, the length in the axial direction of the cylindrical plane is 35 to 70 mm.

The line sensor 30 consists of a solid-state pickup device. For example, the line sensor 30 is formed as an image sensor consisting of a large number of Charge Coupling Devices linearly arranged in an axial direction of the semicylinder defined by the light-emitting surfaces of the second light guides 20. The line sensor 30 picks up the image of the work 28 transferred by a transfer device 33 such as a conveyor in a direction denoted by an arrow 34 in FIG. 1, and the image thus picked up is supplied to an image processing section 36. The signal generated by the line sensor 30 is converted within the image processing section 36 into a binary signal having 256 tones as predetermined standard and, then, forwarded into an inspecting section 38. On the other hand, the signal supplied from the image processing section 36 is processed in the inspecting section 38 on the basis of a predetermined algorithm to automatically inspect whether or not the target object on the surface of the work 28, e.g., the line width of a circuit pattern, is formed to meet the predetermined value and whether or not there is breakage of the wiring or a short-circuit portion.

Figure 4:
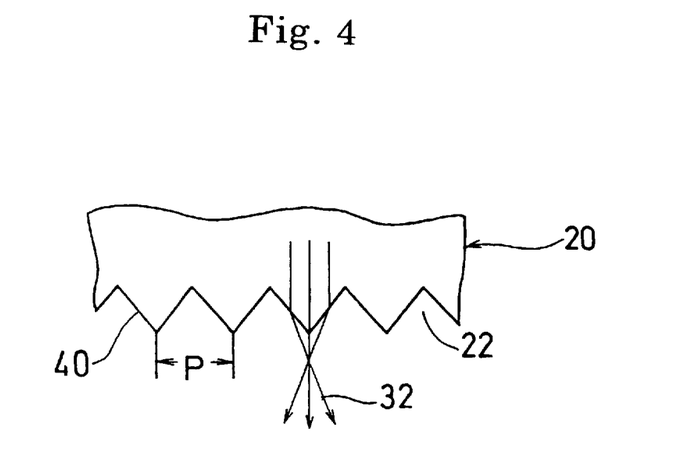
FIG. 4 shows in detail the light-emitting surface of the second light guide.

As shown in FIG. 4, an irregularity 40 shaped like, for example, fine saw teeth is formed on the light-emitting surface 22 of each of the second light guides 20 to make the surface 22 rough. As a result, the light 32 emerging from the light-emitting surface 22 is diffused in the axial direction of the semicylinder defined by the light-emitting surfaces 22 of the second light guides 20. The forming pitch P of the irregularity 40, which varies in response to the size of the target object to be measured, the distance between the work 20 and the light-emitting surface 22, and the like, should desirably be not larger than 50 $\mu m$ in the case where, for example, the line width of the target object is about 3 $\mu m$ and the distance between the work 28 and the light-emitting surface 22, (the radius of the semicylinder) is 0.5 to 1.5 mm. Also, the height, vertical angle and the like of the irregularity 40 can be set at appropriate values by simulation or calculation.

In the line illuminating apparatus 10 of this embodiment, which is constructed as described above, a imaginary semi-cylindrical plane is defined by the light-emitting surfaces 22 of the second light guides 20, and the light rays 32 emerging from the light-emitting surfaces 22 are allowed to mutually overlap each other on the irradiating line L. It follows that, when viewed from the irradiating line L, the brightness is rendered isotropic. As a result, even if an irregularity such as stepped portions or openings are present on the surface of the work 28, bright-dark regions are not formed on the surface of the work 28. This makes it possible to eliminate an erroneous judgment caused by the presence of bright-dark regions derived from the irregularity in the case where an automatic inspection is performed by the inspecting section 38 on the basis of the image picked up by the line sensor 30. Naturally, the accuracy of inspection can be markedly improved. Further, compared with the conventional dome-shaped illumination, the light-emitting surfaces 22 can be arranged in proximity to the irradiating line L to diminish the region to be illuminated. As a result, the brightness required for the inspection can be easily obtained while markedly decreasing the energy loss.

What should also be noted is that, in the embodiment described above, the light-emitting surface 22 consists of a coarsened surface having an anisotropy to permit the emitted light 32 to be diffused in the axial direction of the semicylinder. It follows that, even if light sources (light-emitting surfaces) are not positioned on both end planes of the semicylinder, the brightness in the axial direction of the semicylinder is made uniform by the diffused light to diminish the influences given by the irregularity.

In the embodiment described above, each of the irradiating units 12a and 12b is formed of a plurality of second light guides 20. However, it is possible for each of these irradiating units to consist of a single plate-like light guide. It is also possible to arrange a large number of optical fibers such that the distal ends of these optical fibers define a semicylindrical configuration. In this case, the light emitted from the light source 14 is transmitted directly by these optical fibers such that the irradiating line L is irradiated directly with the light rays emerging from the distal ends of these optical fibers. Further, the embodiment described above covers the case where a printed wiring board constitutes the work 28. However, it is also possible for the work 28 to be replaced by, for example, a glass substrate of a liquid crystal device, a semiconductor chip, a lead frame, or a TAB tape.

Incidentally, it is desirable to arrange a half mirror 42 above the window portion 24 and below the line sensor 30, as shown in FIG. 3 by a dot-and-dash line. In this case, the work 28 is irradiated with the light 44 via the half mirror 42 and the window portion 24. As a result, an effect similar to that obtained by the arrangement of the light-emitting surface can also be obtained in the window portion 24, too, to further diminish the influences given by the irregularity present on the work 28.

Figure 5:
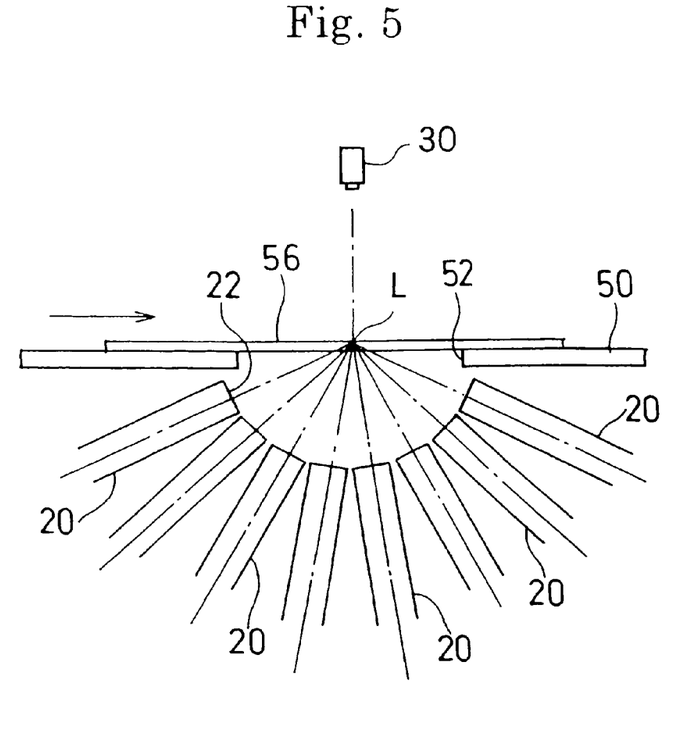
FIG. 5 shows a gist portion of a line illuminating apparatus according to a second embodiment of the present invention.

FIG. 5 shows a gist portion of a line illuminating apparatus according to a second embodiment of the present invention. The apparatus of the second embodiment is applied to an inspecting apparatus that performs inspection by utilizing a transmitted light. To be more specific, the inspecting apparatus comprises an inspecting table 50. A linear opening 52 extending in a direction perpendicular to the paper of FIG. 5 is formed in the inspecting table 50, and the line sensor 30 is arranged above the opening 52. A plurality of plate-like light guides 20 collectively constituting an irradiating unit is arranged below the inspecting table 50. These light guides 20 are arranged such that the light-emitting surfaces 22 collectively define a imaginary semi-cylindrical plane, and the optical axis of the light ray emerging from the light-emitting surface 22 is aligned with the inspecting plane (side surface of the line sensor 30) of a transparent work 56 such as a TAB tape or a glass substrate. The apparatus of the second embodiment constructed as described above also permits producing en effect similar to that produced by the apparatus of the first embodiment.

Figure 6:
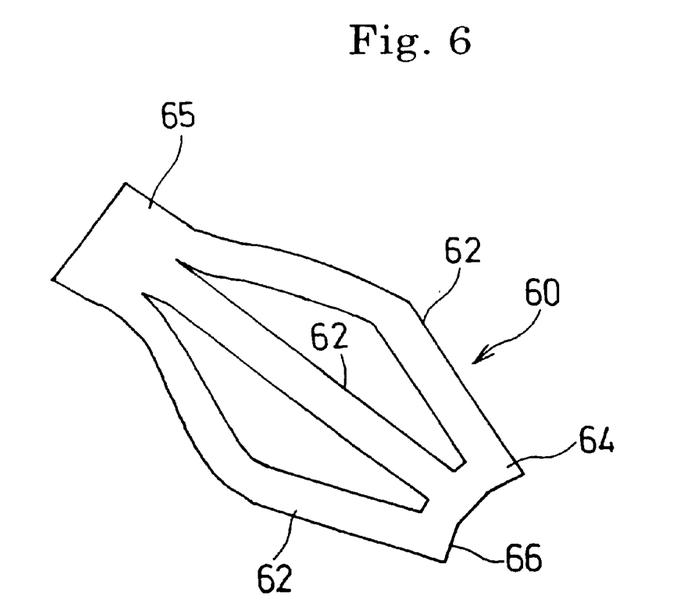
FIG. 6 shows a gist portion of the light guide according to the second embodiment of the present invention.

FIG. 6 shows a second light guide 60 according to the second embodiment of the present invention. The second light guide 60 is made of a resin having a large light transmittance such as an acrylic resin or polycarbonate. The light guide 60 consists of a plurality of plate-like guide portions 62, a light-emitting portion 64 formed by making integral the distal end portions of the guide portions 62, and a light incident portion 65 formed by making integral the proximal end portions of the guide portions 62. In the embodiment shown in the drawing, the second light guide 60 includes three guide portions 62. The end face of the light-emitting portion 64 constitutes a light-emitting surface 66 forming sides of a regular polygon having a width conforming with each of the guide portions 62. Incidentally, it is possible for the light incident portion 65 not to be made integral.

In the light guide 60 of the construction described above, the distal end portions of the guide portions 62 are made integral to form the light-emitting portion 64. The particular construction is effective for facilitating the alignment of the optical axis to make it possible to irradiate the predetermined irradiating line L with the light emerging from the light-emitting surface 66 easily and without fail.

Figure 7:
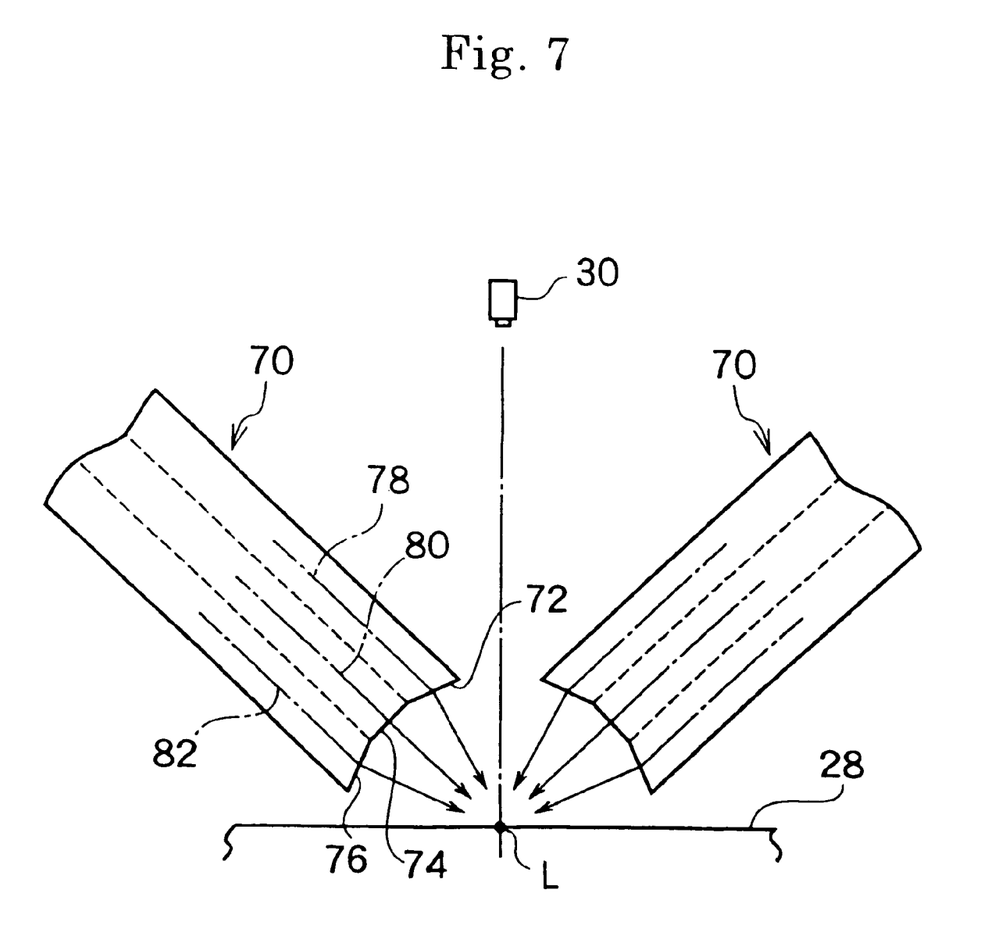
FIG. 7 shows the light-emitting surface of the light guide according to at third embodiment of the present invention.

FIG. 7 shows the light-emitting surface of a light guide 70 according to a third embodiment of the present invention.

The light guide 70 of this embodiment is made of a resin having a large light transmittance such as an acrylic resin or polycarbonate like the light guide in the second embodiment described previously. In the third embodiment, however, the light guide 70 is not divided into a plurality of plate-like members, and the light guide 70 in the form of a single body is disposed such that the distal end surface of the light guide 70 is positioned to face the irradiating line L to guide the light rays to the irradiating line L. A groove having a polygonal cross section is formed at the distal end surface of the light guide 70. A plurality of flat surfaces (three flat surfaces in the drawing) defining the groove perform the function of light-emitting surfaces 72, 74, 76. The optical axes 78, 80, 82 of the light rays supplied through three light guiding passageways partitioned by the ridge lines of the light-emitting surfaces 72, 74, 76 within the light guide 70, said partitioning being represented by broken lines, are parallel within the light guide 70, but are refracted by the inclining angles between the light-emitting surfaces 72, 74, 76 and the optical axes 78, 80, 82 in the light-emitting surfaces 72, 74, 76 to emerge from the light-emitting surfaces. It should be noted that the inclining angles of the light-emitting surfaces 72, 74, 76 relative to the optical axes are adjusted to permit the optical axes 78, 80, 82 emerging from the light-emitting surfaces 72, 74, 76 to cross each other on a single line. In other words, the groove is formed in the distal end surface of the light guide 70 in a manner to substantially conform with an imaginary cylindrical plane formed about the irradiating line L for irradiating the work. Also, the angles of the flat light-emitting surfaces 72, 74, 76 formed in the inner surface of the groove are adjusted to permit the optical axes 78, 80, 82 of the light rays emerging from the light-emitting surfaces to coincide with the center line in the radial direction of the imaginary cylindrical plane.

As shown in FIG. 7, the light guides 70 of the particular construction are arranged on the right side and left side in symmetry with respect to a plane including the center line of the line sensor 30 and the irradiating plane L. By this particular construction, the brightness is rendered isotropic, and the surface of the work 28 can be irradiated with light without bringing about bright-dark portions on the surface of the work 28 even if an irregularity such as a stepped portion or an opening is present on the surface of the work 28 as in the first embodiment described previously. It should also be noted that each of the light-emitting surfaces 72, 74, 76 formed in the groove can be imparted with the irregularity 40 having an inclined surface for diffusing the emitted light in the longitudinal direction of the irradiating line L in this embodiment, too.

As described above, the light-emitting surfaces of the light guides are arranged to define a semicylindrical configuration along the irradiating line L in the present invention, making it possible to shorten the distance between the irradiating plane (plane to be irradiated) and the light-emitting surfaces of the light guides. As a result, the area to be illuminated can be diminished to markedly decrease the energy loss while ensuring the brightness required for the inspection easily and without fail. In addition, since the light-emitting surface is made semicylindrical in a manner to cover the irradiating line L, the brightness as viewed from the irradiating surface is made isotropic, making it possible to prevent various difficulties even if an irregularity such as a stepped portion or an opening is present on the surface of the work such as a semiconductor substrate, a glass substrate of a liquid crystal device, a printed wiring board, a lead frame or a TAB tape. To be more specific, it is possible to prevent generation of bright-dark regions in the irregular portion and to prevent strong reflection of the edge portion of the opening to eliminate incapability of inspection or an erroneous inspection.

Further, the isotropy of the brightness can be further improved by dividing the imaginary semicylindrical plane in the circumferential direction into a plurality of sections each consisting of the light emitting surface of a plate-like light guide. Still further, it is possible to correct the darkness in the axial direction of the imaginary semicylindrical plane by coarsening the light emitting surface in a manner to permit the light emitted from the light emitting surface to be diffused in the axial direction of the semicylinder, thereby to diminish the influences given by the irregularity or opening present on the work.

What is claimed is:

1. A line illuminating apparatus, comprising:

a light source; and a light guide for guiding the light emitted from the light source to a predetermined irradiating line, the light guide having distal ends and defining light emitting surfaces at the distal ends, the light emitting surfaces being arranged in a semi-circular configuration to define a semicylindrical plane covering said predetermined irradiating line.

2. The line illuminating apparatus according to claim 1, wherein said light emitting surfaces are divided in the circumferential direction of said imaginary semicylindrical plane into a plurality of sections each consisting of a plate-like light guide.

3. The line illuminating apparatus according to claim 1, wherein the light emitting surfaces of said light guide are coarsened to permit the emitted light to be diffused in the axial direction of said semicylindrical plane.

4. A line illuminating apparatus, comprising:

a light source; and a light guide for guiding light emitted from the light source to a predetermined irradiating line, the light guide having distal ends and defining light emitting surfaces at the distal ends, the light emitting surfaces are coarsened to permit the light emitted from the distal ends of the light guide to be diffused in an axial direction of a semicylindrical plane;

a light emitting plane at the distal ends of the light guide is arranged in a semi-circular configuration and defines an imaginary semicylindrical plane covering said predetermined irradiating line; and said light emitting plane is divided in a circumferential direction of the semicylindrical plane into a plurality of sections each consisting of a plate-like light guide.

5. The line illuminating apparatus according to claim 1, wherein said light guide consists of a plurality of divided plate-like light guides and is arranged to permit the optical axes of light rays emitted from the light emitting surfaces of the plate-like light guides to be arranged in the radial direction of the semicylindrical plane with the irradiating line positioned in the center line.

6. The line illuminating apparatus according to claim 5, wherein said light guides are arranged in symmetry with respect to the plane including the irradiating line and a line sensor.

7. The line illuminating apparatus according to claim 5, wherein the distal end portions on the side of the light emitting surface of said plate-like light guide are integrally bonded to each other.

8. The line illuminating apparatus according to claim 1, wherein a polygonal groove is formed in the distal end surfaces of said light guide, each surface forming said groove constituting a light emitting surface, and the angles of said light emitting surface are set to permit the optical axes of the light rays emitted from the light emitting surfaces to be adjusted from a direction parallel with said light guide to a direction that is aligned in a radial direction of the semicylindrical plane with the irradiating line set at the center line.

9. A line illuminating apparatus, comprising:

a light source; and a plurality of irradiating units consisting of a plurality of plate-like light guides for guiding light emitted from the light source to a predetermined irradiating line,
wherein said irradiating units are arranged in symmetry with respect to a plane defined by said irradiating line and a sensor directed to said irradiating line;
said light guides have light emitting surfaces formed in distal ends thereof which are arranged in a semi-circular configuration such that light rays emitted from the light emitting surfaces are aligned in a radial direction of an imaginary cylinder with the irradiating line set in a center; and
said light emitting surfaces constitute a coarsened surface having an irregularity including inclined surfaces effective for diffusing the emitted light toward the irradiating line.

10. A line illuminating apparatus, comprising:

a light source; and a plurality of irradiating units consisting of a light guide for guiding light emitted from the light source to a predetermined irradiating line, the irradiating units being arranged in symmetry with respect to a plane defined by said predetermined irradiating line and a sensor directed to said predetermined irradiating line;

a polygonal groove is formed in a distal end surface of said light guide, each surface forming said groove defining light emitting surfaces, and said light emitting surfaces being arranged in a semi-circular configuration to permit optical axes of light rays emitted from the light emitting surfaces to be adjusted from a direction parallel with said light guide to a direction that is aligned in a radial direction of a semicylindrical plane with the predetermined irradiating line set at a center line; and said light emitting surfaces defining a coarsened surface having an irregularity including inclined surfaces effective for diffusing the emitted light toward the predetermined irradiating line.

* * * * *